United States Patent [19]
Hodgson et al.

[11] Patent Number: 5,237,985
[45] Date of Patent: Aug. 24, 1993

[54] UTERINE RETRACTOR

[75] Inventors: James F. Hodgson, Lenexa; Jimmy M. Rowden, Olathe, both of Kans.

[73] Assignee: Crystal Wind, Inc., Lenexa, Kans.

[21] Appl. No.: 901,936

[22] Filed: Jun. 22, 1992

Related U.S. Application Data

[63] Continuation-in-part of PCT/US92/02081 Mar. 16, 1992

[51] Int. Cl.⁵ .............................................. A61B 1/32
[52] U.S. Cl. ...................................... 128/17; 128/20; 606/119
[58] Field of Search ................... 128/17, 20, 23, 3, 7; 606/193, 191, 198, 119; 604/106

[56] References Cited

U.S. PATENT DOCUMENTS

| | | | |
|---|---|---|---|
| 1,856,295 | 5/1932 | Soyatkin | 606/119 X |
| 2,186,143 | 1/1940 | Neugass | 128/23 X |
| 2,456,806 | 12/1948 | Wolffe | 128/3 |
| 3,131,690 | 5/1964 | Innis et al. | 128/23 |
| 3,153,267 | 10/1964 | Rowland, Jr. | 128/16 |
| 3,766,909 | 10/1973 | Ozbey | 128/16 X |
| 3,877,433 | 4/1975 | Librach | 606/119 |
| 3,948,270 | 4/1976 | Hasson | 606/119 X |
| 4,022,208 | 5/1977 | Valtchey | 606/119 X |
| 4,066,071 | 1/1978 | Nagel | 128/7 |
| 4,085,756 | 4/1978 | Weaver | 128/17 X |
| 4,323,057 | 4/1982 | Jamieson | 128/17 |
| 4,430,076 | 2/1984 | Harris | 606/119 X |
| 4,562,832 | 1/1986 | Wilder et al. | 128/20 |
| 4,597,030 | 6/1986 | Brody et al. | 128/20 X |
| 4,627,421 | 12/1986 | Symbas et al. | 128/20 |
| 4,996,974 | 3/1991 | Ciarlei | 128/4 |

FOREIGN PATENT DOCUMENTS 2078526 1/1982 United Kingdom ................. 128/20

Primary Examiner—Richard J. Apley
Assistant Examiner—Karen A. Jalbert

[57] ABSTRACT

A uterine retractor having an elongated insertion rod having at a rear end a ratchet handle which may be rotated. The front end of the insertion rod mounts a retractor finger for rotation substantially perpendicular to the insertion rod in response to rotation of the ratchet handle. The retractor finger which may be inserted within the uterus, upon the insertion of the insertion rod within the vaginal tract of the patient, with the ratchet handle remaining outside of the patient. Movement of the retractor finger, due to movement of the ratchet handle, may thus impart movement to the uterus about two axes, allowing placement of the uterus for medical procedures. The insertion rod may mount a transilluminator in the form of a light source adjacent the front end of the insertion rod. The illumination is visible from the exterior of the vaginal tract, allowing easy location of the cervix, vaginal cuff, and veins and arteries within the vaginal tract.

12 Claims, 7 Drawing Sheets

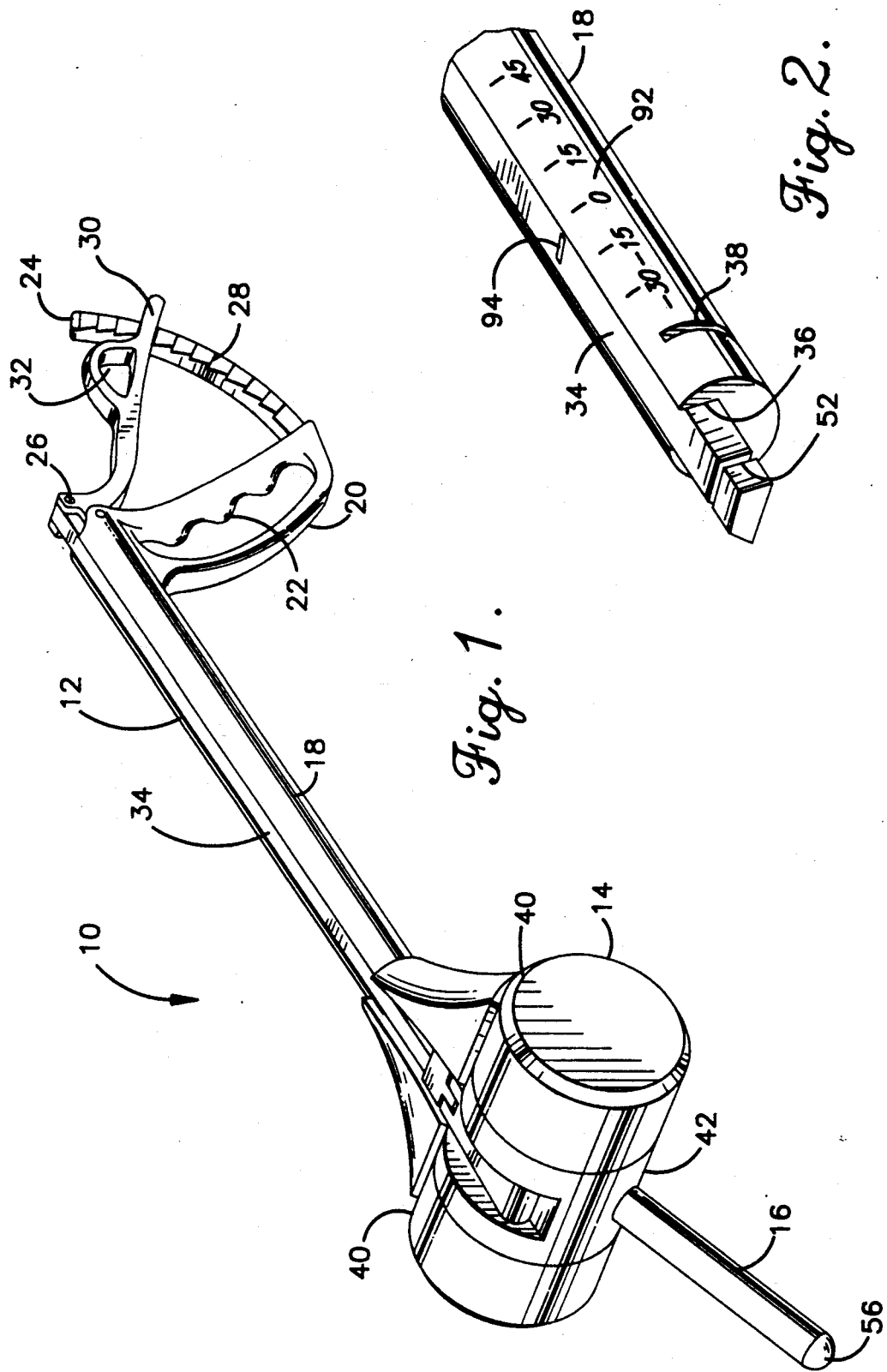

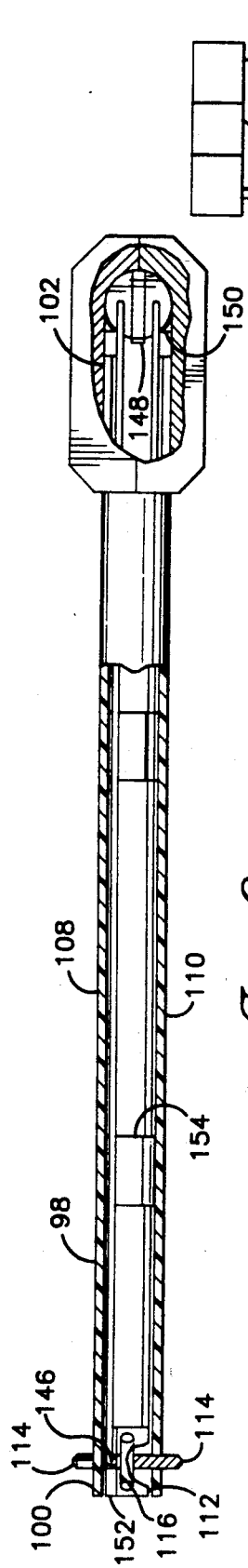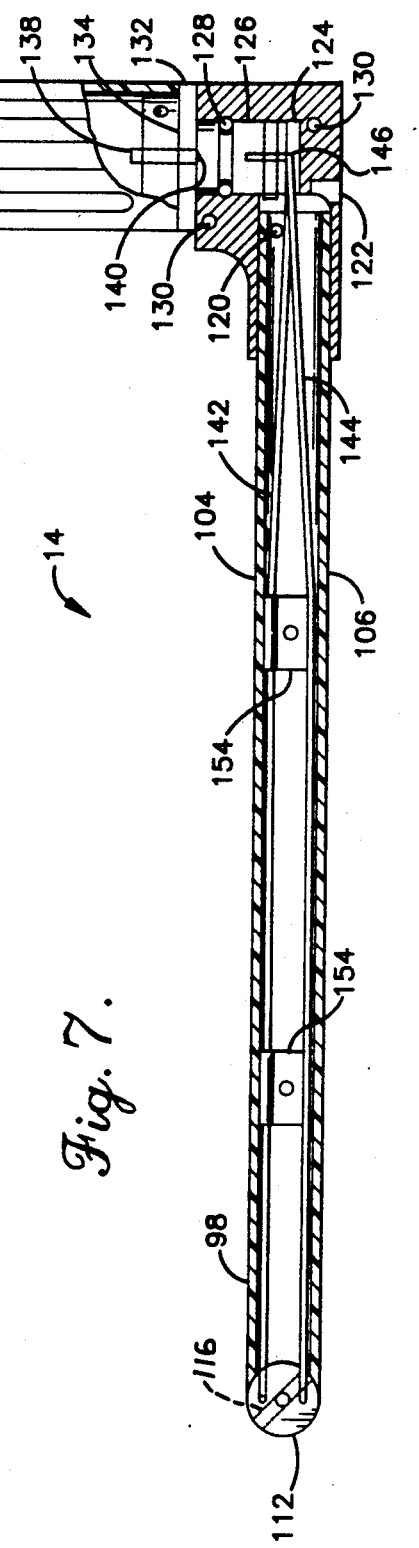

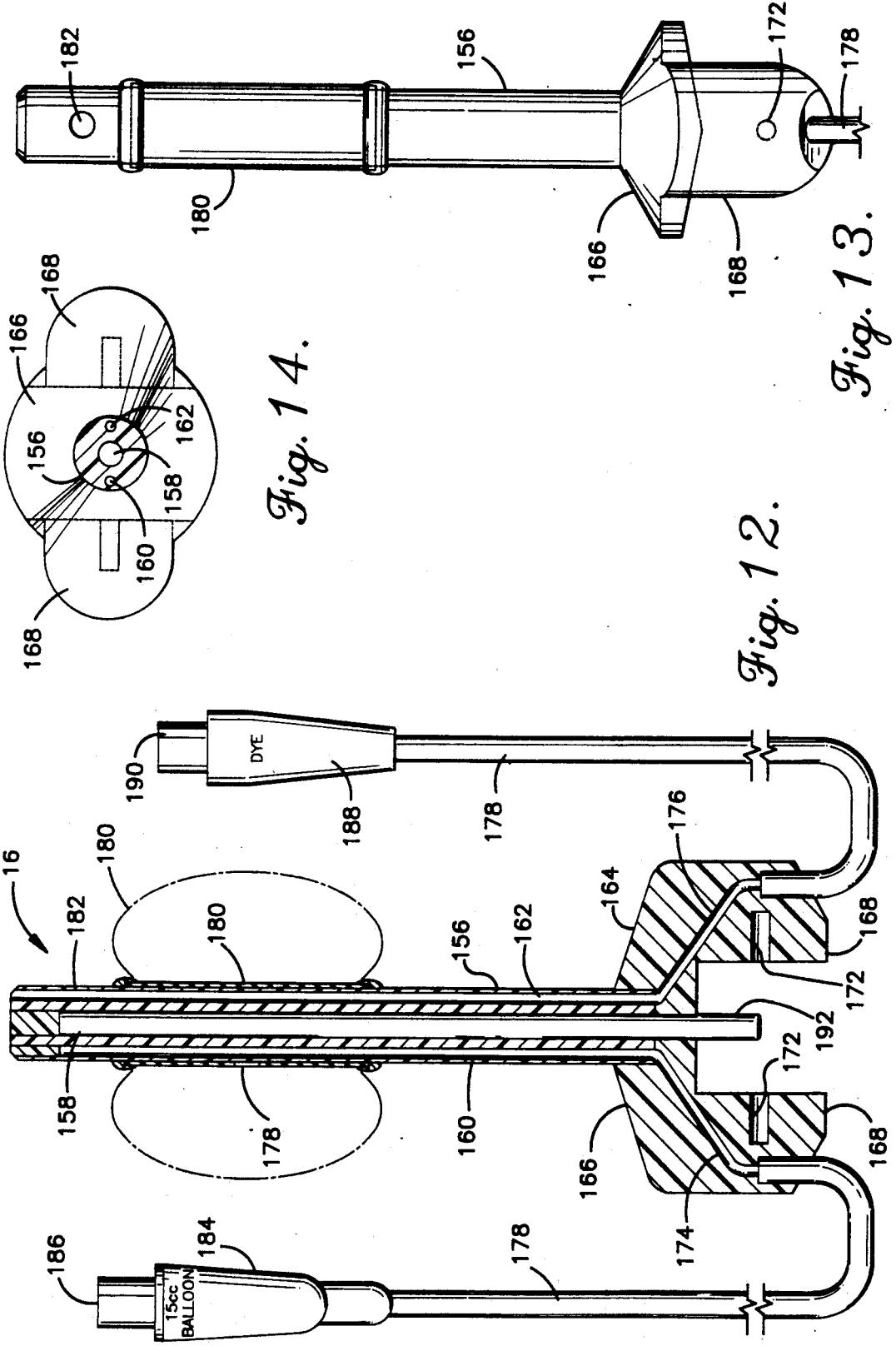

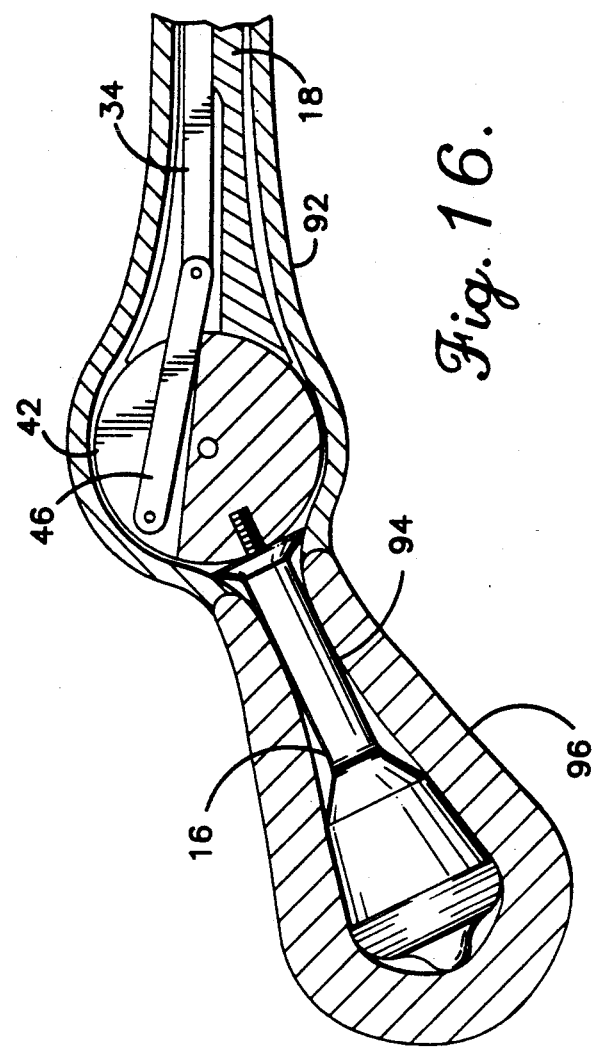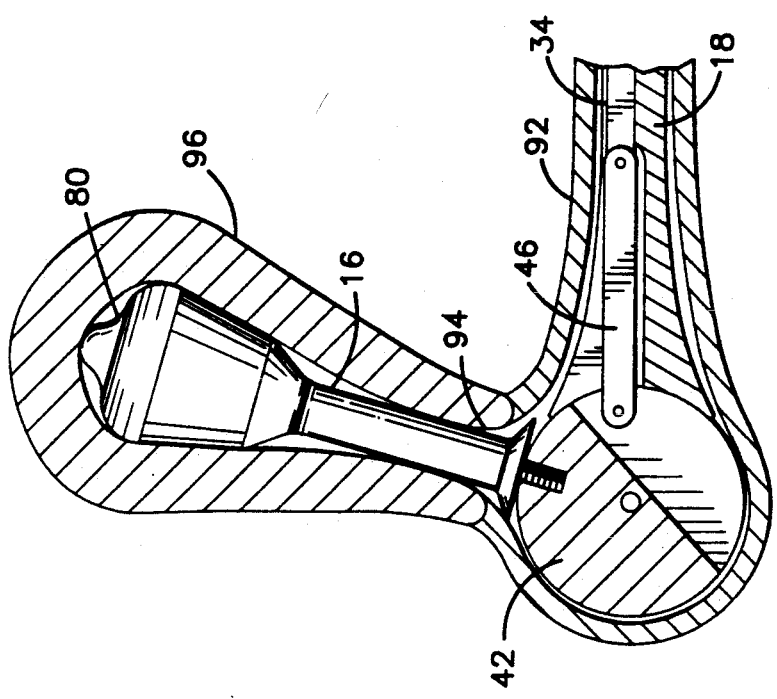

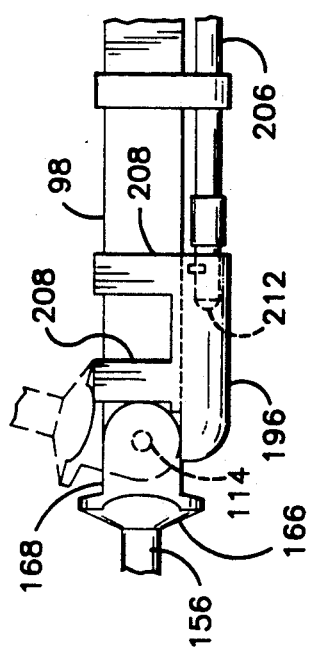
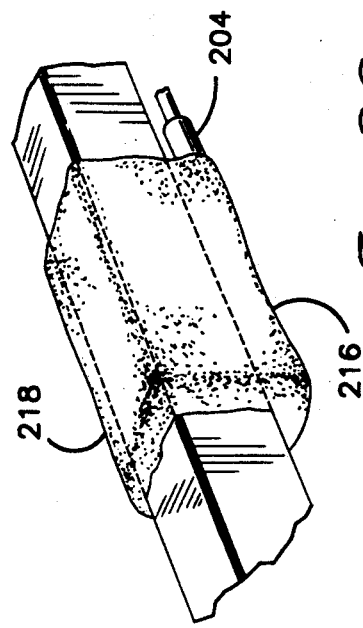
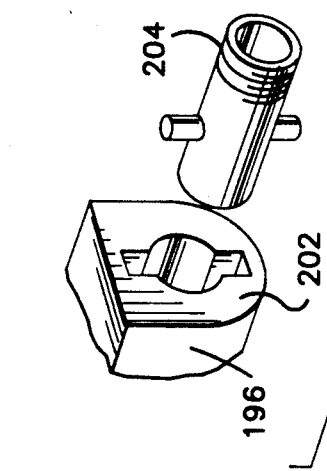
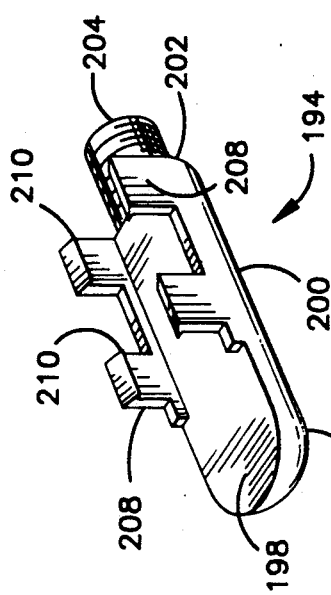
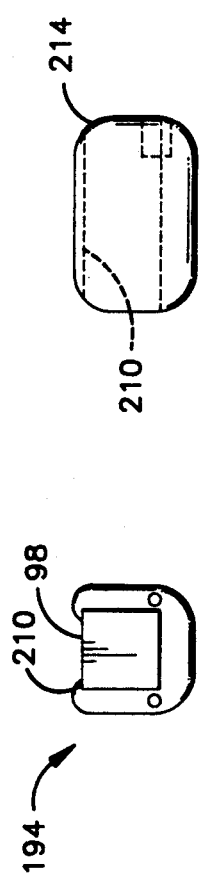
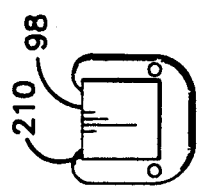

UTERINE RETRACTOR

This application is a continuation-in-part of pending prior application Ser. No. PCT/US92/02081, filed Mar. 16, 1992.

TECHNICAL FIELD

The present invention relates in general to medical devices. In particular, the present invention relates to an improved device for positioning and controlling the uterus, and viewing the vaginal cuff, within the abdominal cavity to aid in medical procedures.

BACKGROUND ART

The uterus of the human female lies within the pelvic region in the abdominal cavity. The uterus essentially consists of a muscular sack opening onto the innermost end of the vaginal cavity. With the exception of this connection to the vagina, the connection to the fallopian tubes near the upper end of the uterus, and a narrow band of fascia connecting the lower lateral portions of the uterus to the pelvic wall, there are no strong connections holding the uterus in place.

Various surgical procedures are performed upon and near the uterus, such as hysterectomy and tubal ligation. During many of these surgical procedures the uterus needs to be moved to various positions to assist in the procedure. The lack of a strong connection between the uterus and other internal organs allows such movement, but effecting such movement has been a source of continuing difficulty.

Additionally, it is at times necessary to determine the position of the cervix and vaginal cuff from the exterior of these organs. However, the coloring and appearance of the exterior of the uterus and the vaginal tract are quite similar. As such it is quite difficult to determine, from the exterior, the position of the cervix and the vaginal cuff.

DISCLOSURE OF INVENTION

An object of the present invention is the provision of a medical device which will allow movement of the uterus to a desired position, in more than two dimensions, and maintain the uterus in this position.

Another object of the present invention is to provide such a device which may firmly and safely maintain the uterus in the desired position.

Yet another object of the present invention is to provide such a device which may allow for hydrotubation.

A further object of the present invention is to provide such a device which will assist in the location, from the exterior, of the cervix and the vaginal cuff.

These and other objects are achieved by a uterine retractor having an elongated insertion rod having at a rear end a ratchet handle which may be rotated. The front end of the insertion rod mounts a retractor finger for rotation substantially perpendicular to the insertion rod in response to rotation of the ratchet handle. The retractor finger may be inserted within the uterus, upon the insertion of the insertion rod within the vaginal tract of the patient, with the ratchet handle remaining outside of the patient. Movement of the retractor finger, due to movement of the ratchet handle, may thus impart movement to the uterus about two axes, allowing placement of the uterus for medical procedures. The insertion rod may mount a transilluminator in the form of a light source adjacent the front end of the insertion rod.

The illumination is visible from the exterior of the vaginal tract, allowing easy location of the cervix, vaginal cuff, and veins and arteries within the vaginal tract.

BRIEF DESCRIPTION OF THE DRAWINGS

The objects and features of the invention noted above are explained in more detail with reference to the drawings in which like reference numerals denote like elements, and in which:

FIG. 1 is a perspective view of a first embodiment of a device according to the present invention;

FIG. 2 is a detail perspective view of a portion of the device of FIG. 1;

FIG. 6 is a bottom view in partial cross-section of a third embodiment of the device according to the present invention;

FIG. 7 is a side view in partial cross section of the device of FIG. 6;

FIG. 12 is a front view in partial cross section of a further embodiment of a retractor finger according to the present invention;

FIG. 13 is side view of the finger of FIG. 12;

FIG. 14 is a cross sectional view along line 14—14 of FIG. 12;

FIGS. 15 and 16 are cross-sectional side views showing operation of the first embodiment of the device;

FIG. 17 is a perspective view of a first embodiment of a vaginal transilluminator according to the present invention;

FIG. 18 is a detail perspective view of the device of FIG. 17;

FIG. 19 is a side view of the device of FIG. 17 mounted upon the device of FIGS. 6 and 7;

FIG. 20 is a front view of a second embodiment of a transilluminator;

FIG. 21 is a side view of the device of FIG. 20; and

FIG. 22 is a perspective view of a third embodiment of a transilluminator.

BEST MODE OF CARRYING OUT THE INVENTION

Figure 3:
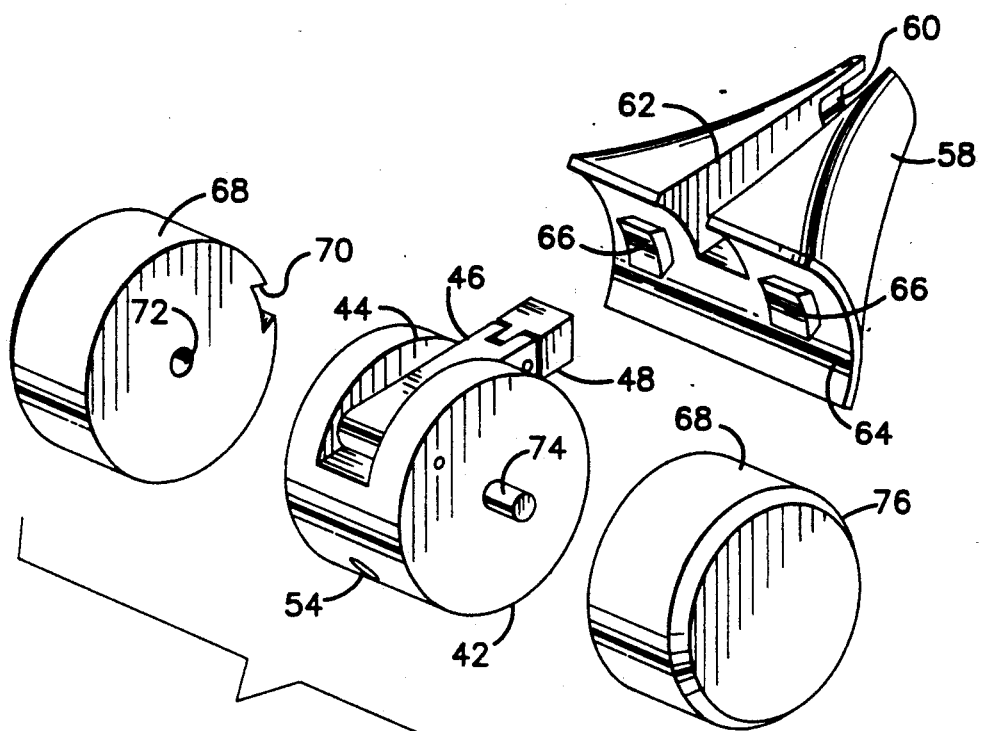
FIG. 3 is an exploded side view of the retractor assembly of FIG. 1.

With reference to FIG. 1, a first embodiment of the device according to the present invention is generally designated by reference numeral 10. The device 10 generally consists of an actuator grip 12, a retractor housing 14 and a retractor finger 16.

The actuator grip 12 is preferably of a form commonly employed for various medical devices, such as surgical scissors, clamps, etc. The grip 12 includes an elongated support rod 18 which includes an integral handle grip 20 at a first end thereof. The handle grip 20 may include various protrusions 22 to improve control of the handle grip when it is manually grasped. Extending rearward from a lower end of the handle grip 20 is a catch member 24. The catch member 24 extends in an arc about a pivot axis 26 adjacent the intersection of the handle grip 20 and support rod 18. The catch member 24 includes a plurality of pawls 28 along at least one side thereof.

The pawls 26 are adapted to engage a lower end of a trigger 30 which pivoted to the axis 28 adjacent an upper end of the trigger. The pawls 28 will engage with the trigger 30 to prevent movement of the trigger relative to the catch member in at least one direction. The trigger 30 may include an extending through hole 32 adapted to receive the user's thumb therethrough and act as a thumb grip to allow the trigger 30 to be drawn rearward away from the handle grip 20. Alternatively, or additionally, a spring could be provided for biasing the trigger rearward of the handle grip. This could be affected by use of a coil spring extending between these two members, preferably formed as a coil spring extending about the axis 26 and engaged between the members 20 and 30.

The upper end of trigger 30 extends beyond axis 26 and is pivoted to a slide rod 34 slidably mounted upon support rod 18. As is best shown in FIG. 2, it is preferred that the support rod 18 have a roughly circular exterior configuration (in cross-section) and include a slide cavity 36 extending longitudinally through the length of the support rod 18. This slide cavity receives the slide rod 34. To ensure that the slide rod is maintained within the slide cavity 36, it is preferred that these elements have appropriate mating configurations, such as a trapezoidal configuration shown in FIG. 2.

As may be readily seen, pivotal movement of the trigger 30 about axis 26 will result in sliding movement of the slide rod 34 with respect to support rod 18. It is this relative sliding movement which is employed in the present device to effect movement of the retractor finger 16 with respect to the retractor housing 14.

The retractor housing 14 is mounted upon a second end of the support rod 18 and is fixed with respect thereto. The mounting of the retractor housing to the support rod may be permanent, in which case various portions of the retractor housing may be made monolithic with the support rod, or the retractor housing may be removably mounted upon the support rod 18. For such a removable mounting the second end of the support rod may include a circumferential catch groove 38 extending about a portion of the outer periphery of the support rod which will receive a mating ridge of the retractor housing. Other arrangements allowing removal of the housing could of course be employed, such as exterior threads on the support rod which engage with a threaded collar on the housing, etc.

The retractor housing extends forwardly of the second end of the support rod 18 to a pair of lateral pivot blocks 40. The pivot blocks 40 are spaced from each other and provide a pivotal mount for a retractor pivot 42 which is mounted between the pivot blocks. The retractor pivot is mounted for rotation about an axis substantially perpendicular to the longitudinal axis of the support rod 18.

Figure 4:
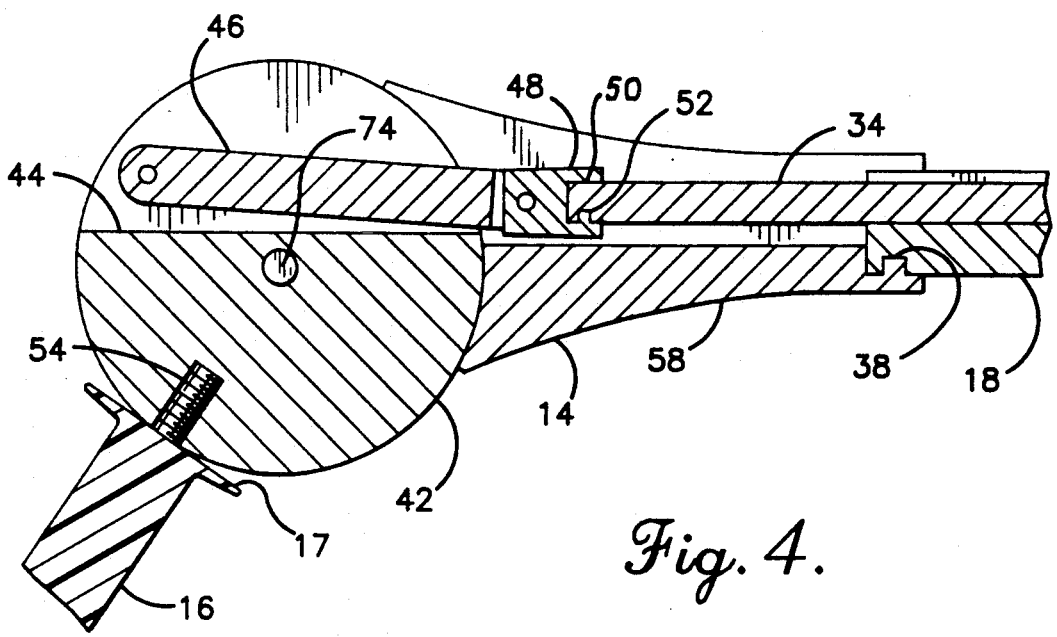
FIG. 4 is a partial side view in cross-section of the device of FIG. 1.

With particular reference to FIG. 4, it will be seen that at least a portion of the periphery of the retractor pivot 42 is substantially circular such that it may freely pivot with respect to housing 14. A laterally central portion of ratractor pivot 42 is removed along a chord spaced from the pivot axis of pivot 42 to define a channel 44. Within channel 44 a first end of a swing arm 46 is pivoted to the retractor pivot about an axis substantially perpendicular to the longitudinal axis of the support rod 18, at a point spaced from the pivot axis of pivot 42. The swing arm 46 extends rearward from this connection to the retractor pivot 42 and is connected at its second end to the slide rod 34.

As may be readily envisioned from FIG. 4, relative movement of the slide rod 34 will cause movement of swing arm 46, thus causing rotation of retractor pivot 42. Since the swing arm 46 is pivoted to the retractor pivot 42 at a position spaced from the pivot axis of member 42, vertical motion will be imparted to the first end of the swing arm. If such vertical movement were imparted to the slide rod 34, this could cause binding within the slide cavity 36, restricting movement of the slide rod. To overcome this difficulty, it may be necessary to provide the second end of swing arm 46 with a pivotal connection to the slide rod. This may be effected by various means, for example by use of a coupling 48.

The coupling 48 is pivoted to the second end of swing arm 46 about an axis substantially perpendicular to the longitudinal axis of support rod 18. The other end of coupling 48 will include means for connecting with the slide rod 34. This may be by means of a coupling cavity 50 which is sized to receive the second end of slide rod 34. Where the retractor housing 14 is removably mounted upon the support rod 18, the coupling 48 must be removably mounted to slide rod 34. To affect this, the second end of slide rod 34 may be provided with a peripheral groove 52, similar to catch groove 38 on the support rod, and the interior of the coupling cavity 50 include a mating ridge which will be removably received within groove 52. To allow the ridge of the coupling to fit over the end of the slide rod 34, an appropriate slit (not shown) extending perpendicular to the ridge may be provided. Of course, where the pivot housing is provided integral with the support rod 18 the swing arm 46 need not be removable from the slide rod 34. In such situations the second end of swing arm 46 may be pivoted directly to slide rod 34, as is shown in FIGS. 15 and 16.

The cuter periphery of retractor pivot 42 includes a finger mounting hole 54. Mounting hole 54 extends radially inward of the retractor pivot and includes appropriate means, such as internal threads, to removably mount the retractor finger 16. The retractor finger 16 is an essentially elongated member preferably having a rounded free end 56 and means at the other end, such as a threaded bolt 55, for engagement with the mounting hole 54.

Regardless of whether the retractor housing 14 is removable from the support rod 18, it is preferable that the device be capable of partial disassembly for cleaning after use. One such arrangement to effect cleaning is shown in FIG. 3. As is shown in this figure, the retractor housing 14 is formed as a main housing 58 having a cavity 60 adapted to receive the support rod 18. The main housing 58 also includes a swing arm channel 62 extending from the cavity 60 outwardly to a mounting face 64. As should be apparent, the swing arm channel will house the swing arm 46 and allow its communication between the retractor pivot 42 and slide rod 34.

The mounting face 64 includes a pair of chamfer blocks 66 extending outwardly therefrom. As is shown in FIG. 3, the chamfer blocks taper inwardly towards the mounting face 64 when viewed from the side. The chamfer blocks each serve to mount an associated pivot support 68. Each pivot support may be a substantially cylindrical member having an outer diameter substantially equal to that of the retractor pivot 42, such that these elements form a substantially continuous cylindrical surface. In such a case the outer peripheral edges of each pivot support are preferably provided with smooth transitions 76 to reduce sharp edges and thus the possibility of damage to the vaginal tract.

Each pivot support 68 includes a trapezoidal channel 70 at a position on the periphery thereof, and opening onto the interior planar face, which will mate with the associated chamfer block 66. The chamfer block 66 and channels 70 may be provided with appropriate grooves and ridges, as with grooves 38 or 52, such that the pivot supports will be securely retained in place during use of the device.

It should of course be apparent that various other means of attaching the pivot supports to the main housing could be employed, such as a threaded hole in the pivot support which receives a bolt extending through the main housing. The particular manner of attaching the pivot supports is not critical, and is determined by ease of manufacturing, security of attachment and ability to disassemble for cleaning.

Each of the pivot supports 68 also includes a substantially centrally located pivot hole 72 adapted to receive a pivot rod 74 extending outwardly from the planar faces of the retractor pivot 42. As may be readily envisioned, the retractor pivot will be held in place by the pivot rods 74 received within the pivot holes 72 while the pivot supports are maintained in position upon the chamfer blocks 66. As such, the retractor housing 14 may be at least partially disassembled for cleaning. The pivot rods could of course be formed on the pivot supports, with the retractor pivot 42 having pivot holes 72, or the pivot rods could be formed by a single long rod extending through the pivot supports and retractor pivot.

It is also possible to avoid the use of pivot supports entirely. For example an arrangement similar to a standard hinge could be employed for pivoting the retractor pivot to the main housing. In such an arrangement both the retractor pivot and main housing could have one or more integrally formed through holes, each offset in their longitudinal direction such that they combine to define a single through hole. A hinge pin would then be inserted through this hole and be releasably retained therein. As such, it should be apparent that various means of forming the pivotal connection could be employed.

The elements of the retractor housing 14 may be formed of any material suitable for the purpose. For example, rugged plastics or metals may be employed. With the increase in the use of surgical lasers, it is preferred that the exterior of the retractor housing 14 include a matte finish, possibly black. This will avoid reflection of the laser and aid in determining when an incision has been made completely through the vaginal walls, during procedures which require such incisions.

Figure 5:
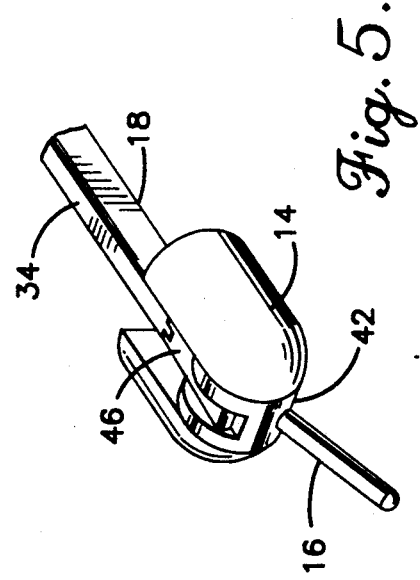
FIG. 5 shows a second embodiment of the device according to the present invention.

It should be apparent to those skilled in the art that various modifications may be made to the device. For example, the retractor housing 14 may take various shapes other than the substantially cylindrical configuration shown, such as a shape as shown in FIG. 5, where the lateral sides of the housing and the retractor pivot 42 are formed such that the forwardmost end is a portion of a sphere, with a transition into a generally circular configuration in a plane perpendicular to the longitudinal axis of the support rod. This arrangement may provide a more natural shape for entry into the vaginal tract and provide less scraping damage thereto.

Another embodiment of the retractor is shown in FIGS. 6 and 7. In this embodiment there is no separable actuator grip and housing, and as such the portion of the device shown in these figures is designated as a retractor housing 14. The housing 14 includes an insertion rod 98 elongated along a longitudinal axis and having a first end 100 and a second end 102. The rod 98 preferably has a substantially square hollow cross section, defined by top and bottom faces 104 and 106 and left and right lateral or side faces 108 and 110.

The side faces are elongated at the first end 100 such that they extend beyond the top and bottom faces and define drum mounting flanges. The mounting flanges include a laterally extending drum mounting hole. A drum 112 having the general form of a cylinder is mounted between the drum mounting flanges by a pair of pivot pins 114 which extend through the associated mounting hole into the drum at a through hole substantially coincident with the longitudinal axis of the cylinder forming drum 112. The outer diameter of the drum is substantially equal to the outer dimension between the top and bottom faces 108 and 110, and the ends of the mounting flanges are preferably rounded to this diameter such that the first end of the rod and the drum form a smooth unit. The drum 112 further includes a finger hole 116 extending perpendicular to, and including, the longitudinal axis of the drum. The finger hole assists in mounting the finger 16 as will be better described below.

The second end of the insertion rod 98 is fixed to a collar mount 118. The collar mount is generally L-shaped with a rod hole opening into a first leg and receiving the rod 98 therein. As best shown in FIG. 6, the collar mount is formed as two halves and these halves are each fixed to the rod 98 by means of screws 120. Alignment pin 130 may be employed to retain the relative positions of the halves of the collar mount when assembled. A cleaning hole 122 may extend from the exterior of the collar to the interior of the insertion rod 98 to more easily allow cleaning fluids to pass into the interior of the rod.

The second leg of the collar mount includes a pivot hole 124 which opens into this leg and is in communication with, and substantially perpendicular to, the rod hole. Pivot hole 124 is substantially circular in cross-section and receives a ratchet rod 126 having the form of a cylinder. As may be envisioned, the attached rod may rotate within the pivot hole. An appropriate peripheral groove 128 may be formed in the ratchet rod, with a pair of pins extending between the halves of the collar mount and received within this groove to prevent translation of the ratchet rod along its longitudinal axis with respect to the collar mount.

The ratchet rod extends to the exterior of the collar mount, and is there fixed to a ratchet collar 132 having a reduced diameter section spaced from the collar mount and thus defining an upwardly facing shoulder 134. Mounted to this shoulder is a ratchet handle 136 having a sufficient size that it may be readily manipulated by hand. The exterior of the handle may include appropriate knurling or facets to improve friction.

Also mounted to the ratchet collar at a position radially spaced from its axis of rotation is a spring plunger 138, biased downward into contact with the upper face of the collar mount. This upper face includes a plurality of circumferentially spaced depressions 140 adapted to receive the plunger 138. The plunger and depressions thus cooperated to form a detente to releasably maintain the handle in various angular positions with respect to the collar mount.

Rotation of the handle 136 is intended to cause rotation of the drum 112, and to this end there are provided first and second tension wires 142 and 144. While the wires could have a sufficient diameter that a limited compression load could be transferred, it is only necessary that the wires be sufficiently strong in tension, as will become apparent. Each of the wires includes first and second ends, each having a bent portion 146. The bent portions are respectively received within appropriate holes in the drum 112 and rachet rod 126, in directions substantially parallel to the longitudinal axes of the drum and ratchet rod. In particular, the bent portions at the first ends of the wires are received within the drum 112 on opposite sides thereof with the bent portions extending towards one another. The bent portions on the second ends are received within the free end of the ratchet rod and extend in a common direction.

As may be seen, the bent portions are radially spaced from the axes of rotation, such that rotation of the handle 136 with respect to the collar mount will cause rotation of the ratchet rod 126, thus causing the second ends of the wires to undergo movement having a component in the direction of the longitudinal axis of the insertion rod 98. As the wires are not formed of an elastic material, this results in similar movements of the first ends of the wires, causing the drum to rotate with respect to the insertion rod. It should be apparent that although a slight compressive force will be placed on one of the wires during rotation, the other wire will be in tension and provide all necessary force transmission. As may be envisioned, fixing the finger 16 to the rotatable drum will allow the desired rotational movement of the finger 16 as in the previous embodiment.

Also as in the previous embodiment, the extent of this drum rotation is approximately 130 degrees. This is best measured by use of the finger hole 116. In particular, when the finger hole is parallel to the longitudinal axis of the insertion rod the device is in the unflexed condition. From such position it is preferred to allow approximately 20 degrees rotation away from the handle 136 (retroflexed), and the remainder of the rotation being towards the handle (antroverted). The spring plunger 138 and depressions 140 are properly located to form detente stops within the handle rotation which produces such rotation of the drum.

It is also necessary to provide limit stops to define the ends of the drum rotation. This may be achieved by providing a limit pin 148 extending radially from the ratchet rod 126, and a pair of appropriately located protrusions 150 within the collar mount, such that the limit pin will abut against the protrusions at the limits of the desired rotation. Additionally or alternatively, the drum may be provided with flats 152 at its longitudinal ends. The flats are appropriately formed such that the wires 142 will abut against the flats at the limits of rotation.

This embodiment of the housing may be formed of many materials, but is preferably formed entirely, or at least in the majority, of stainless steel. This will allow the housing to have a long life, and allow it to be placed within an autoclave for cleaning between uses.

The retractor finger 16 will now be described in detail.

Figure 8:
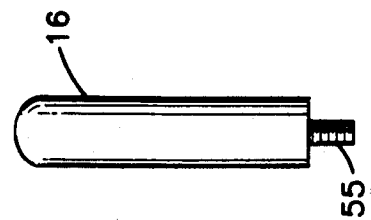

As shown in FIG. 8, a first embodiment of the retractor finger 16 may consist essentially of an elongated solid member, having an exterior diameter of approximately 3 mm. While the finger 16 of FIG. 8 has been shown as extending in a substantially straight line, it is possible to form the finger 16 with curvatures such that it does not extend directly radially outward from the retractor pivot 42.

Figure 9:
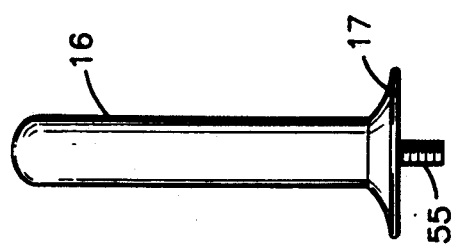

The retractor finger may be provided with a guard flange 17 near the lower end thereof, as shown in FIG. 9. This flange will prevent the finger from fully entering the uterus, due to abutment between the flange and the patient's cervix. Use of such a flange will ensure a known insertion depth for the finger, so that it does not perforate or injure the fundus, or other portions, of the uterus. The maximum width of flange 17 may be on the order of 20 mm, with the finger remaining approximately 3 mm in diameter. It is preferred that the finger and flange be formed as a monolithic unit.

To ensure that the uterus is maintained in the desired position, it is an important aspect of the present invention to provide the retractor finger 16 with means to expand and contract the finger adjacent the free end thereof. This expansion should be sufficient such that the finger contacts the interior of the uterus, reducing or eliminating movement of the uterus with respect to the finger.

Figure 10:
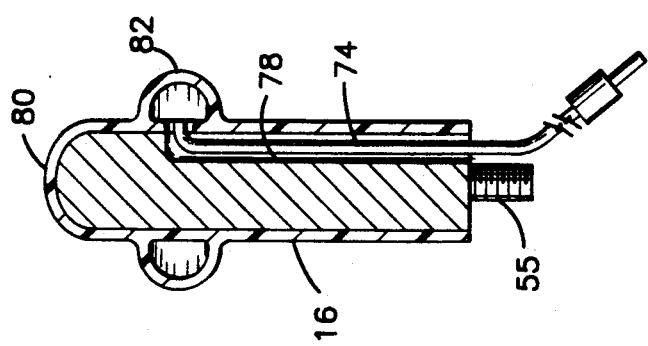

One means for effecting this is shown in the embodiment of FIG. 10. In this embodiment, the finger 16 includes a longitudinally extending groove 78 along at least a portion of the length thereof. Mounted over the finger 16 is a sheath 80 formed of a resilient material. The sheath 80 includes a circumferentially extending pocket 82 which is connected to the exterior by a catheter 84 (not shown in cross section for clarity) which extends within the groove 78.

In its initial configuration, the sheath 80 will conform closely to the exterior of finger 16 and a such provide little increase in its outer dimensions, allowing easy insertion of the finger. As the catheter 84 is located within groove 78, there is no longitudinal protuberance along the side of the finger where the catheter runs. Once the finger 16 has been inserted through the cervix and is located within the uterine cavity, a saline solution, air, inert gas or other material may be pumped through the catheter 84 and into the pocket 82. Due to the resilient nature of sheath 80, this will result in expansion of the pocket, increasing the sheath (and therefore the finger) diameter at this point. Once withdrawal of the finger 16 from the uterine cavity is desired, the fluid, air or other material within pocket 82 may be removed therefrom, causing the resilient sheath 80 to collapse to a diameter substantially corresponding to that of finger 16.

The use of the flange 17 in conjunction with the expandable finger provides excellent advantages. These elements work together to maintain the uterus in position upon the finger. This in turn allows the finger to be moved such that the uterus is placed in the proper position and reliably maintained in this position.

Figure 11:
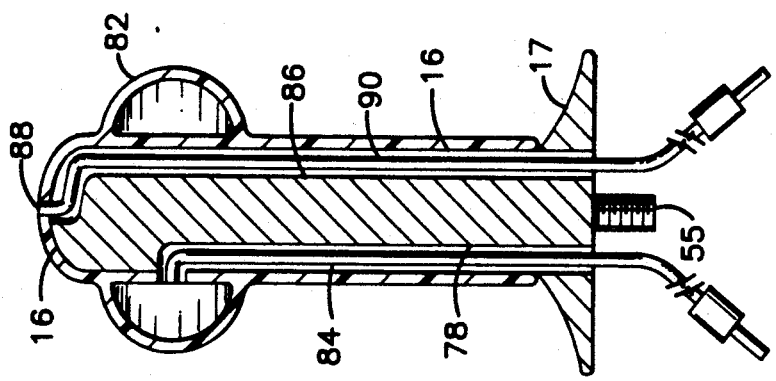
FIGS. 8-11 show embodiments of retractor fingers according to the present invention.

In yet another embodiment shown in FIG. 11, the features of the embodiment of FIG. 10 are retained, but finger 16 is additionally provided with means to effect hydrotubation. In this arrangement the finger 16 is provided with a second groove 86 extending longitudinally thereof to a point above or below the anticipated position of pocket 82. The sheath 80 will include an opening 88 which is connected to a second catheter (also not shown in cross section for clarity) which is run along the second groove 86 to the exterior of the patient, similar to catheter 84.

When hydrotubation is desired, saline solution, a dye in saline solution, or other material may be passed through second catheter 90 to be expelled from the opening 88. As should be apparent to those skilled in the art, various openings could be provided within sheath 80 with appropriate communication via catheters or subcatheters running within associated grooves in the finger 16.

The finger 16 may be reusable, but it is preferred that it be a one-time or disposable member. Where the finger is provided with the sheath 80 (having pocket 82, opening 88 or both), they may be provided as a single unit for one-time use, or the finger may be reused with a new sheath.

The fingers of the above embodiments may be formed of a variety of materials, including plastics and metals. As with the housing 14, it may be preferable to provide the exterior of finger 16 with a matte finish.

A further, and preferred, embodiment of the finger 16, adapted for use on the housing of FIGS. 6 and 7, is shown in FIGS. 12-14.

This embodiment includes a main shaft 156 elongated in the longitudinal direction and having a free front end and a rear end. Extending longitudinally through the main shaft are a centrally located main hole 158, and first and second lateral lumens 160 and 162. The main shaft may be formed as an extrusion of approximately 50 Durometer silicone, although other material could be employed. A suitable adhesive is placed within the main hole 158 and first lumen 160 at the free end of the main body to seal these elements for reasons made clear below.

A main body 164 is fixed to the rear end of the main shaft 156. As is best shown in FIG. 13, main body 164 includes a radially extending flange portion 166 closest to the free end of the main shaft, in a manner similar to the above embodiments, and further includes a body hole 170 which is coincident with, and of substantially the same diameter as, the main hole 158 in main shaft 156. The flange portion mounts a pair of laterally spaced, opposed and rearward extending pivot ears 168. Pin holes 172 extend into the inner opposed face of each of the pivot ears 168. As will be made more apparent below, the pin holes are of a size and shape to readily receive the pivot pins 114 on the retractor housing 14.

First and second extension tubes 174 and 176 extend through the main body 164 and are in communication with associated ones of the first and second lumens 160 and 162. Each of the extension tubes may include a protective outer sheath 178. Such sheaths preferably have inner ends which are received within the main body to ensure protection of the extension tubes.

The main body may be formed by insert molding using a silicone of approximately 80 Durometer, or other material having the appropriate strength and flexibility. An appropriate pin is first inserted into the rear portion of the main hole 158 to ensure formation of the body hole 170. Next the extruded main shaft 156 with extension tubes 174 and 176 (with protective sheaths 178) in communication with the associated lumens, may be placed within a mold and held in position thereby. The silicone would then be injected into the mold to form main body 164 as a monolithic unit fixed to the main shaft 156.

As in the previous embodiments, it is preferred that this finger include an expansible pocket. To this end, a lateral balloon hole 178 is formed from the exterior of the main shaft 156 to the first lumen 160 at a position spaced rearward from the free end. A sleeve 180 of resilient expansible material such as extruded silicone is then placed over the exterior of the main shaft 156 so that the balloon hole 178 is substantially intermediate the longitudinal ends of sleeve 180. These longitudinal ends are sealed to the main shaft, preferably by use of an appropriate adhesive 181. The use of such an adhesive may also provide a smooth transition between the main shaft diameter and the sleeve diameter.

As may be readily envisioned, introduction of a pressurized gas or fluid through the first extension tube 174 will cause the gas or fluid to travel through the first lumen 160, through the balloon hole 178 and into the space between the sleeve 180 and the exterior of the main shaft 156, causing the sleeve 180 to expand to the position shown by dashed lines in FIG. 12. In such expanded position the exterior of the expanded sleeve 180 will contact the interior of the uterus as is better described below.

Also as in the embodiments described above, hydrotubation may be performed with this embodiment. Specifically, the lack of an adhesive plug at the free end within the second lumen 162 ensures that material traveling from the second extension tube 176 through the second lumen 162 will exit from the main shaft 156. To guard against the possibility of this single exit opening of the second lumen being blocked, there may be provided a dye hole 182 extending laterally into the second lumen 162 at a position spaced rearward of the free end of the main shaft, but forward of the sleeve 180.

To aid in use of the device, it is preferred that the free ends of the extension tubes 174 and 176 include appropriate connectors and indicia. Specifically, the free end of first extension tube 174 may be provided with a shrink wrap cover 184 having appropriate indicia identifying this extension tube as leading to the expansible balloon, and preferably also including an indication of the volume necessary to fully inflate the balloon. This free end of the first extension tube would also include an appropriate connector 186 such as a tube receiver with a Halkey Roberts check valve.

In a similar manner, the free end of the second extension tube 176 includes a cover 188 with appropriate indicia indicating that it leads to the hydrotubation exits 182. An appropriate connector 190 such as a Luer lock may also be provided.

In operation with the retractor housing 14 of FIGS. 6 and 7, the finger 16 is first provided with a reinforcement rod 192. The rod 192 has an outer diameter slightly greater than that of the main hole 158 extending through shaft 156. The rod 192 is thus inserted into the main hole 158 with a tight friction fit and to such an extent that the rear end of the reinforcement rod extends outwardly from the main body 164 a distance slightly beyond the pin holes 172.

The rod 192 could be formed as a portion of the finger 16 as it is provided to the user, or the rod could be reusable and inserted on site. In either event, the resilient nature of the main shaft 156 and relative diameters of the reinforcement rod and main hole allow the reinforcement rod to be securely retained without the use of adhesives or other means. In particular, attempts to pull the main shaft 156 from the reinforcement rod will cause the main shaft to extend longitudinally, and thus contract radially. This will provide a tighter grip upon the reinforcement rod such that removal of the rod is quite difficult.

Once the shaft and rod are associated, the housing 14 of FIGS. 6 and 7 is grasped by the user and the handle 136 rotated until the finger hole 116 is readily accessible. The finger 16 is then moved towards the drum 112 such that the rear end of rod 192 enters the finger hole 116. During this insertion the pivot ears 168 may be manually forced outward until the free ends of the pivot pins 114 may be inserted into the pin holes 172. The resilient nature of the main body 164 will then cause the pivot ears to move back to their original position, thus capturing the pivot pins within the pin holes 172. As may be readily envisioned, this capture of the pivot pins will prevent movement of the finger 16 away from the drum 112, while the insertion of the rod 192 within the drum 112 will assure that the finger 116 rotates with the drum 112 in a manner similar to the previous embodiments.

As noted above, the flange prevents excessive insertion of the finger which may damage the uterus. Since there is variation in the size of the uterus from individual to individual, it is preferred that the finger be provided in a number of lengths, such as four. For assurance of the proper size, the different sizes may each be assigned a particular color.

This arrangement may be further enhanced by a modification of a standard prior art tool used for uterine sounding, the procedure employed for determining the size of the uterus. This prior art tool consists of an elongated thin rod which is inserted through the cervix into the uterus, until the end of the rod touches the fundus of the uterus. Mounted on the rod is a collar which may slide with difficulty along the rod, and which has a exterior diameter greater than the cervix.

This collar will abut against the cervix as the rod is inserted, and will slid along the rod. Upon withdrawal of the rod from the patient, the position of the collar on the rod provides an indication of the size of the uterus. To aid in choosing the proper size of finger 16, this rod may be modified to include several color bands at longitudinal positions, corresponding to the different colored sizes of finger 16. The physician therefore need only match the color of the finger to the color on the rod at the position of the collar.

The operation of the present device is best illustrated with reference to FIGS. 15 and 16. In each of these figures the device 10 has been inserted within the vaginal tract 92 of the patient and the retractor finger 16 inserted through the cervix 94 to be located within the cavity of uterus 96. In each of these figures, the finger 16 has been provided with a sheath 80, with the pocket 82 thereof having been inflated to maintain the device in proper position.

In the position of FIG. 15, the trigger 30 has been pivoted towards the handle grip 20, causing the slide rod 34 to move rearward with respect to support rod 18. This rearward movement is transmitted to the swing arm 46, causing it to move rearward also, thus causing the retractor pivot 42 to be moved clockwise (in FIG. 15). As the retractor finger 16 is fixed to the retractor pivot 42, the finger 16 is also rotated clockwise, bringing the device into the most anteverted position and moving the uterus towards the symphysis pubis or pelvic bone, and upward out of the abdominal cavity.

It should be apparent that in this position the surgeon will have excellent visualization of, and access for operation upon, the uterus, the fallopian tubes and other organs during surgical procedures The uterus in this position lies well away from the other abdominal organs, such as the bowel, reducing the possibility of injury to these other organs during procedures. This position has been found to greatly facilitate surgery in this area, especially using laproscopic techniques.

It should also be noted that the device 10 may be rotated about the longitudinal axis of support rod 18 to thus move the uterus laterally to the left or right of the midline plane when in the position shown in FIG. 15. This rotation is easily accomplished by manual movement of the handle grip, which is exterior of the patient. In addition to allowing greater visualization, this will extend the fascia and blood vessels which extend between the sides of the uterus and the pelvic wall. This greatly facilitates procedures on this area, and is an important aspect of the present invention.

In the position shown in FIG. 16, the trigger 30 has been moved rearward away from the handle grip 20, thus causing the slide rod to move forward with respect to the support rod 18. As above, this motion will be transmitted to the swing arm 46 causing the retractor pivot 42 to be moved counter-clockwise from the position of FIG. 15. This will in turn cause the retractor finger 16 to be moved counter-clockwise, causing the uterus to move downward within the abdominal cavity towards the rectum and into its most retroflexed position. As before, the device 10 may be rotated about the longitudinal axis to provide left or right movement of the tip of the uterus.

The amount of angular movement of the retractor pivot 42, and thus the finger and uterus, is dependent upon the geometry of the device, i.e. the placement of the pivot points, length of the swing arm, etc. It is preferred, however, that the device be capable of approximately 115° of movement between the most anteverted position and the most retroflexed position.

An important aspect of the present invention is the provision of the pawls 28 which engage with the trigger 30, allowing the retractor pivot to be located securely at numerous angular positions between these extremes. Various other arrangements could be employed for maintaining the trigger in place, such as a screw arrangement.

For an accurate indication of the angular position of the finger with respect to the support rod, the support rod 18 may be provided with appropriate markings or indicia 92 (FIG. 2) which cooperate with a hash mark 94 upon the slide rod 34. The position of the hash mark 92 with respect to the indicia 93 may thus indicate the position of the finger. (While elements 92 and 94 have been indicated as adjacent the second end of the slide and support rods in FIG. 2, it is to be understood that the elements 92 and 94 must be placed sufficiently close to the handle assembly 20 such that they will not be obscured by placement within the vaginal tract when the device is in use.)

As should be apparent, the embodiments of FIGS. 6, 7 and 12-14 would operate in a similar manner. The main difference would be the action used to effect rotation of the finger 16, which in these embodiments would be the rotation of handle 136.

A transilluminator attachment for use in combination with the present device is shown in FIGS. 17-19, and is generally designated by reference numeral 194. Device 194 essentially consists of a body 196 having a substantially planar face 198 adapted to abut against a lower face of the insertion rod 98 (or the support rod 18) and an outer surface 200 having smooth transitional curves. The body 196 is formed of a material which will transmit light, and may be transparent or translucent. Suitable materials for the body 196 include plexiglass or Lexan.

A rear end 202 of the body 196 includes a coupling 204 to allow attachment of a light source, if necessary. Coupling 204 may be of a type commonly employed to retain the terminal of a fiber optic waveguide 206 (FIG. 19) used to transmit light. The coupling will allow the waveguide to be in optic communication with the body 196 such that the body 196 is illuminated by the light transmitted through the wave guide 206.

As is best shown in FIG. 18, the coupling 204 may be removable from the body 196. The mounting arrangement between the body and the coupling may take many forms, such as a bayonet arrangement. The removable mounting of the coupling will allow the body 196 to be a disposable unit while the coupling 204 may be reused. This is because the coupling 204 will typically be formed as a metal which may withstand the heat of an autoclave, while the materials forming the body 196 may typically not be sterilized by such a treatment.

The body 196 includes appropriate means to releasably retain the body to the insertion rod 98. For example, the main body could include one or more pair of laterally opposed legs 208. The legs 208 are preferably monolithic with the body 196 and include inwardly extending catch faces 210 adapted to engage with the upper face of the insertion rod 98. The upper ends of the legs 208 may include appropriate inclined surfaces to aid in the resilient expansion of the legs about the width of insertion rod, with the material forming the body 196 being chosen partially for such resilience.

The device 194 is preferably located adjacent the drum 112. To this end, the legs 208 and the forwardmost extent of the body 196 may be of such dimensions that placing the device on the insertion rod with the forwardmost set of legs 208 in sliding engagement with the pivot ears 168 of the finger 16, as shown in FIG. 19, will result in the forward end of the body 196 being in the proper position. This will aid in proper and expedient mounting of the device 194.

The use of a transillumination device 194 is to form a source of illumination within the vagina for a purpose described in more detail below. As such, various light sources could be employed. However, fiber optic waveguides are known in the surgical arts, and are preferred due to the lack of possibly damaging heat generated by such illumination.

It is also possible to provide various arrangements to increase the illumination provided by body 196. For example, the planar upper face 198 may be provided with a mirror coating such that light impinging upon this face is reflected outward. It is also possible to provide the cavity receiving the coupling 204 with an appropriate shape defining a lens 212 to better direct the illumination provided by the wave guide. The choice of materials will also have an effect upon the transmitted light, as will the exterior finish, for example a satin finish, provided on the outer surface 200.

As may be readily envisioned, the body 196 mounted upon insertion rod 98 shown in FIG. 19 will provide a good source of light immediately below and to a slight lateral extent of the insertion rod. However, there may be situations where it is preferred to provide a more even illumination about the bottom and both lateral sides of the insertion rod. Such an arrangement could be provided by a second embodiment of the body 196 shown in FIGS. 20 and 21. In this arrangement, the body 214 is generally U-shaped and has a substantial thickness about both the bottom face and the right and left side faces of the insertion rod 98. As in the previous embodiment, catch faces 210 may be provided along the upper ends of the lateral or side portions Of the body 214 to removably retain the body upon the insertion rod. To ensure that adequate illumination is provided about the circumference of the body 214, there may be provided two cavities retaining couplings 204, with these cavities being located adjacent the lower lateral corners of the insertion rod.

Yet another embodiment of the transillumination device 194 is shown in FIG. 22. In this embodiment, the device includes a body 216 having a coupling 204 as in the previous embodiments, but in this embodiment, the body 216 includes a monolithic sheath 218 which completely surrounds the insertion rod 198. In particular, the body 216 and sheath 218 are formed of an optically clear material which is additionally elastic, such as an optical grade silicone. The sheath 218 would be placed upon the rod 98 prior to mounting of the finger 16, with the sheath 218 being expanded to pass about and beyond the pivot pins 114, and the elastic nature of the material forming the device thereafter contracting to securely maintain the device in position upon the insertion rod.

From the above discussions of the transillumination device, it should be apparent to those skilled in the art, that various modifications may be made in the shape of such devices. For example, the body of the embodiment shown in FIG. 17 could be provided with laterally extending protrusions adjacent the front face to provide greater lateral illumination in the area closest to the drum.

The operation of the present transillumination device will now be described with reference to FIGS. 15, 16, and 19.

When employed upon the retractor housing 14 of FIGS. 6 and 7, the transillumination device according to the present invention will be spaced slightly rearward of the flange portion 166 of the finger 16. As such, when the device 10 of such embodiment is inserted within the uterus and vagina in a manner similar to that shown in FIGS. 15 and 16, the flange portion 166 will abut against the cervix, while the transillumination device 194 is located within the vagina adjacent the cervix, in abuttment with the anterior vaginal fornix or posterior vaginal fornix.

When the uterus and vagina are viewed from the exterior (i.e., from the interior of the abdominal cavity) there is little color differentiation or other indication of the point at which the cervix is located, and in particular, the location of the vaginal cuff. With the present transillumination device, however, the light emitted by the body 196 passes through the tissue of the vagina and may be readily seen from the exterior of the vagina. Such transillumination may be extremely useful for the location of veins and arteries, since such veins and arteries are backlit by such illumination device, and easily viewed. Additionally, the location of the illumination device adjacent the drum 112, and thus the cervix, will provide a readily discernable indication of the location of the cervix and vaginal cuff. Furthermore, the transillumination will outline the vagina anatomically beneath the urethera and bladder so as to aid in the correct placement of sutures in procedures such as retopubic urethropexy.

While the larger embodiments of FIGS. 20 and 21 will provide greater lateral extent of such transillumination, it may not be necessary in all procedures. This is due to the ability of the present device 10 to be rotated about the midline axis of the patient, thus causing movement of the illumination device about such axis. Additionally, the handle 136 may be moved until the finger 16 extends substantially parallel to the longitudinal axis of the insertion rod 98, and the entire retractor housing 14 rotated 180° about the insertion rod such that the illumination device is moved a similar amount within the vagina. While such an arrangement is useful, the location shown in FIG. 19 will typically be sufficient, as the antroverted position of the finger shown in dashed lines will cause stretching of the vaginal cuff and provide greatest access to such area, with that same area being provided with the greatest illumination by the transillumination device 194.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

We claim:

1. A uterine retractor, including:
    an elongated insertion rod having a longitudinal axis and first and second ends, said first end adapted to be inserted within a vagina of a patient;
    a drum mounted at said first end and adapted for rotation about a drum axis substantially perpendicular to said insertion rod;
    a handle mounted to said second end and extending substantially perpendicular to said longitudinal axis, said handle being mounted for rotation about a handle axis substantially perpendicular to said longitudinal axis;
    means for causing rotation of said drum with respect to said insertion rod about said drum axis in response to rotation of said handle with respect to said insertion rod, said means including at least one tension wire extending within said insertion rod and having a first end connected to said drum at a position spaced from said drum axis and a second end connected to said handle at a position spaced from said handle axis; and
    means for mounting a retractor finger, said means including a pair of pivot pins, each of said pins extending outwardly from said insertion rod in opposite directions along a common axis substantially coincident with said drum axis, and a finger hole extending at least partially into said drum along a line perpendicular to, and including, the longitudinal axis of the drum.

2. A retractor as in claim 1, wherein said pivot pins are rigidly connected to said drum and extend through said insertion rod, to thereby mount said drum for said rotation about said drum axis.

3. A retractor as in claim 1, wherein said at least one tension wire comprises two said tension wires, said first ends and second ends being circumferentially spaced about said drum and said handle, respectively.

4. The uterine retractor of claim 1, in combination with a transilluminator, said transilluminator comprising:
    an illuminable body; and
    means for mounting said body to said retractor housing at a position in proximity to said means for mounting a retractor retractor.

5. In combination, a retractor as in claim 1 and a retractor finger, said finger comprising:
    a main shaft elongated along a shaft axis, said shaft having a first end adapted to be inserted through the cervix and into the uterus, and a second end;
    a main body connected to said main shaft at said second end thereof, said main body having a dimension, perpendicular to said shaft axis, greater than that of said main shaft to thereby define an abutment for placement against the cervix;
    a pair of pivot ears extending from said main body away from said first end of said main shaft parallel to, and in spaced opposition about, said shaft axis, said pivot ears each including a pin hole perpendicular to, and opening toward said shaft axis and receiving an associated one of said pivot pins of said retractor; and
    an at least substantially rigid reinforcement rod extending along at least a portion of the length of said main shaft and beyond said main body to a free end located between said pivot ears and received within said finger hole of said drum of said retractor.

6. The combination of claim 5, wherein said pivot pins are rigidly connected to said drum and extend through said insertion rod, to thereby mount said drum for said rotation about said drum axis.

7. The combination of claim 5, wherein said at least one tension wire comprises two said tension wires, said first ends and second ends being circumferentially spaced about said drum and said handle, respectively.

8. The combination of claim 5, wherein said retractor finger includes means permitting ejection of fluids therefrom.

9. The combination of claim 5, wherein said retractor finger further includes a selectively expandable portion adjacent said first end, said expandable portion adapted to prevent unintentional removal of said finger from the uterus of the patient, and further including means permitting expansion and contraction of said expandable portion.

10. A retractor finger adapted for use with a uterine retractor, comprising:
    a main shaft elongated along a shaft axis, said shaft having a first end adapted to be inserted through the cervix and into the uterus, and a second end;
    a main body connected to said main shaft at said second end thereof, said main body having a dimension, perpendicular to said shaft axis, greater than that of said main shaft to thereby define an abutment for placement against the cervix;
    a pair of pivot ears extending from said main body away from said first end of said main shaft parallel to, and in spaced opposition about, said shaft axis, said pivot ears each including a pin hole perpendicular to, and opening toward said shaft axis; and
    an at least substantially rigid reinforcement rod extending along at least a portion of the length of said main shaft and beyond said main body to a free end located between said pivot ears.

11. A retractor finger as in claim 10, wherein said retractor finger includes means permitting ejection of fluids therefrom.

12. A retractor finger as in claim 10, wherein said retractor finger further includes a selectively expandable portion adjacent said first end, said expandable portion adapted to prevent unintentional removal of said finger from the uterus of the patient, and further including means permitting expansion and contraction of said expandable portion.

* * * * *